United States Patent

(12) United States Patent
Hotta

(10) Patent No.: US 9,989,461 B2
(45) Date of Patent: Jun. 5, 2018

(54) MEASURING DEVICE AND NON-TRANSITORY COMPUTER READABLE MEDIUM

(71) Applicant: FUJI XEROX CO., LTD., Tokyo (JP)

(72) Inventor: Hiroyuki Hotta, Kanagawa (JP)

(73) Assignee: FUJI XEROX CO., LTD., Minato-ku, Tokyo (JP)

( * ) Notice: Subject to any disclaimer, the term of this patent is extended or adjusted under 35 U.S.C. 154(b) by 161 days.

(21) Appl. No.: 15/200,286

(22) Filed: Jul. 1, 2016

(65) Prior Publication Data

US 2017/0045447 A1    Feb. 16, 2017

(30) Foreign Application Priority Data

Aug. 12, 2015 (JP) ................. 2015-159804

(51) Int. Cl.
*G01D 5/34* (2006.01)
*G01N 21/47* (2006.01)

(52) U.S. Cl.
CPC ..... *G01N 21/4785* (2013.01); *G01N 21/4738* (2013.01); *G01N 2201/0633* (2013.01); *G01N 2201/0636* (2013.01); *G01N 2201/0638* (2013.01)

(58) Field of Classification Search
CPC ............... G01N 21/4785; G06T 7/80
See application file for complete search history.

(56) References Cited

U.S. PATENT DOCUMENTS

2008/0117440 A1* 5/2008 Saendig ............. G01D 5/24438
356/617
2011/0194035 A1    8/2011 Aizawa et al.

FOREIGN PATENT DOCUMENTS

| JP | 2001-194614 A | 7/2001 |
| JP | 2010-108566 A | 5/2010 |
| JP | 2011-186434 A | 9/2011 |

* cited by examiner

*Primary Examiner* — Thanh Luu
(74) *Attorney, Agent, or Firm* — Sughrue Mion, PLLC

(57) ABSTRACT

A measuring device includes a light-emitting unit that radiates light onto an object, a first lens that changes a divergence degree of the light, a diaphragm having an aperture that reduces a diameter of the light, a second lens that converges and radiates the light onto the object, a light-receiving unit that receives at least part of the light that has been reflected by the object and that has passed through the second lens, a measuring unit that measures the object by using results related to the light-receiving unit, a reflector whose angle with respect to the light is adjustable, and a correction unit that varies a light-receiving position on the light-receiving unit by varying the reflector's angle and corrects a light amount of the light-emitting unit and a sensitivity of the light-receiving unit by using results obtained at each light-receiving position.

8 Claims, 11 Drawing Sheets

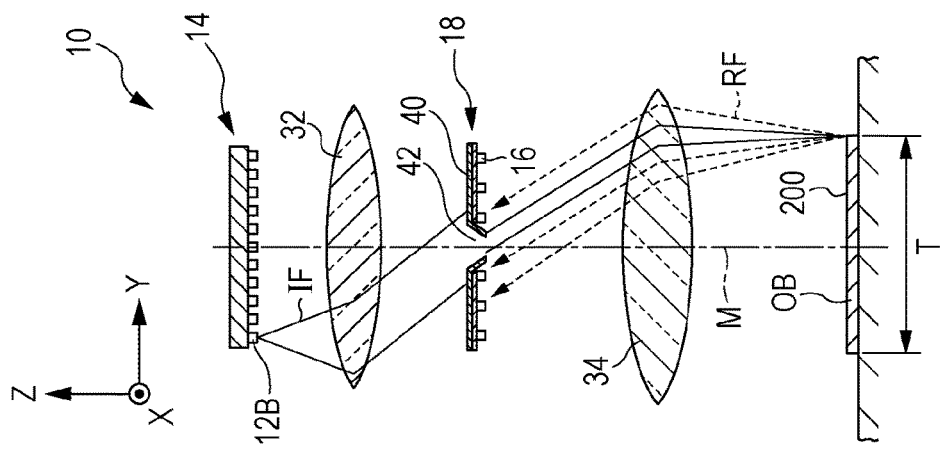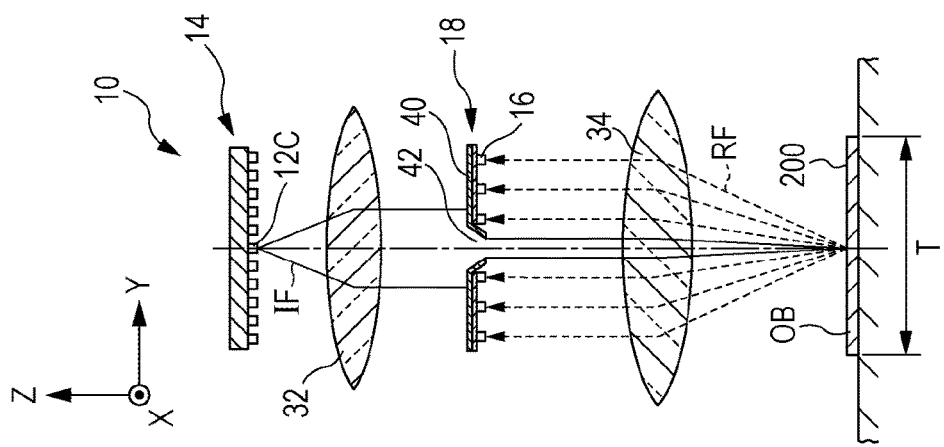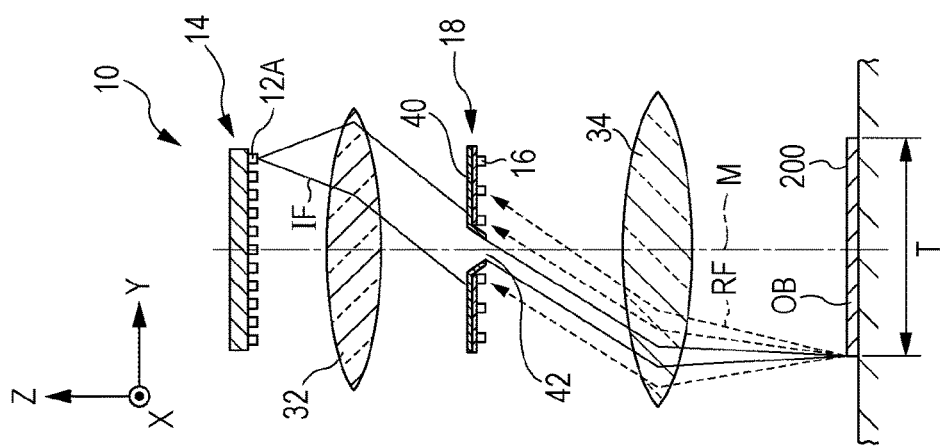

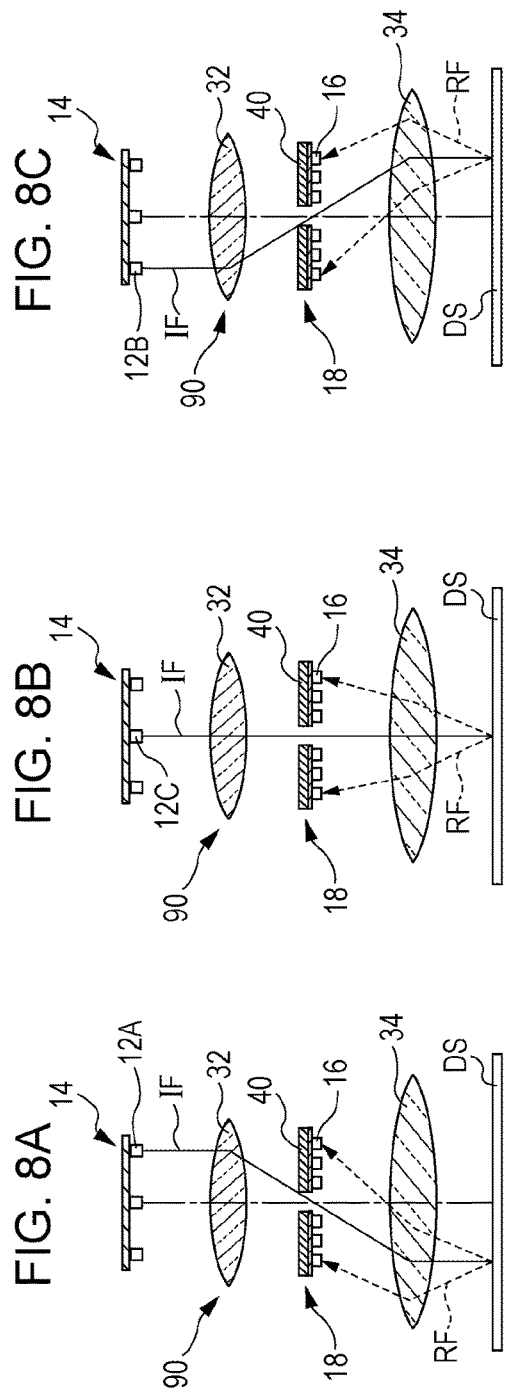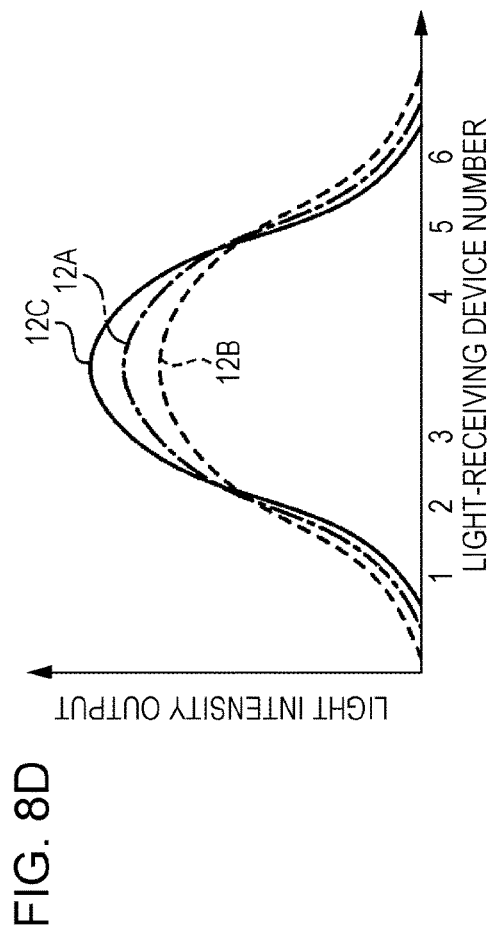

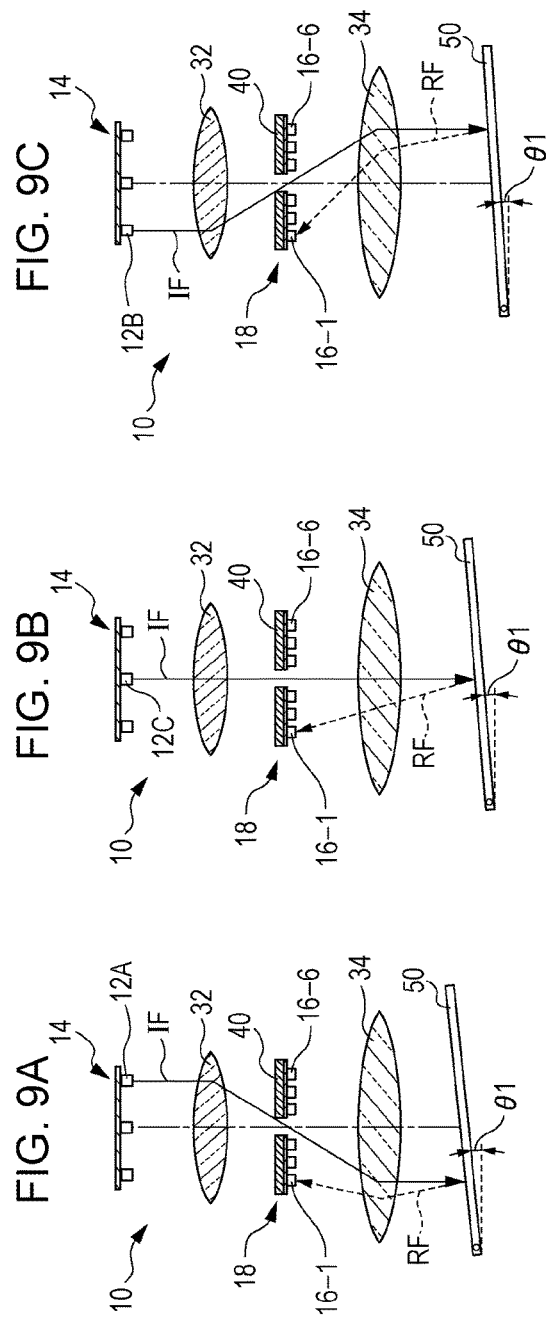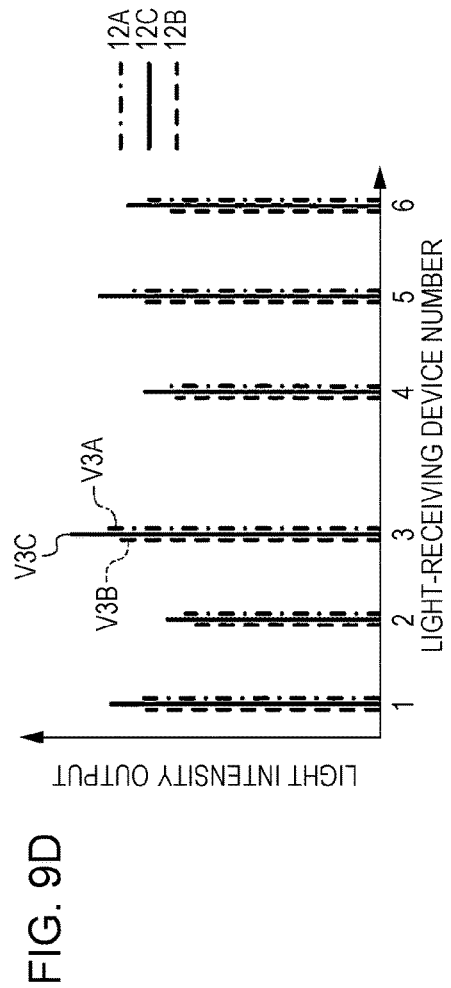

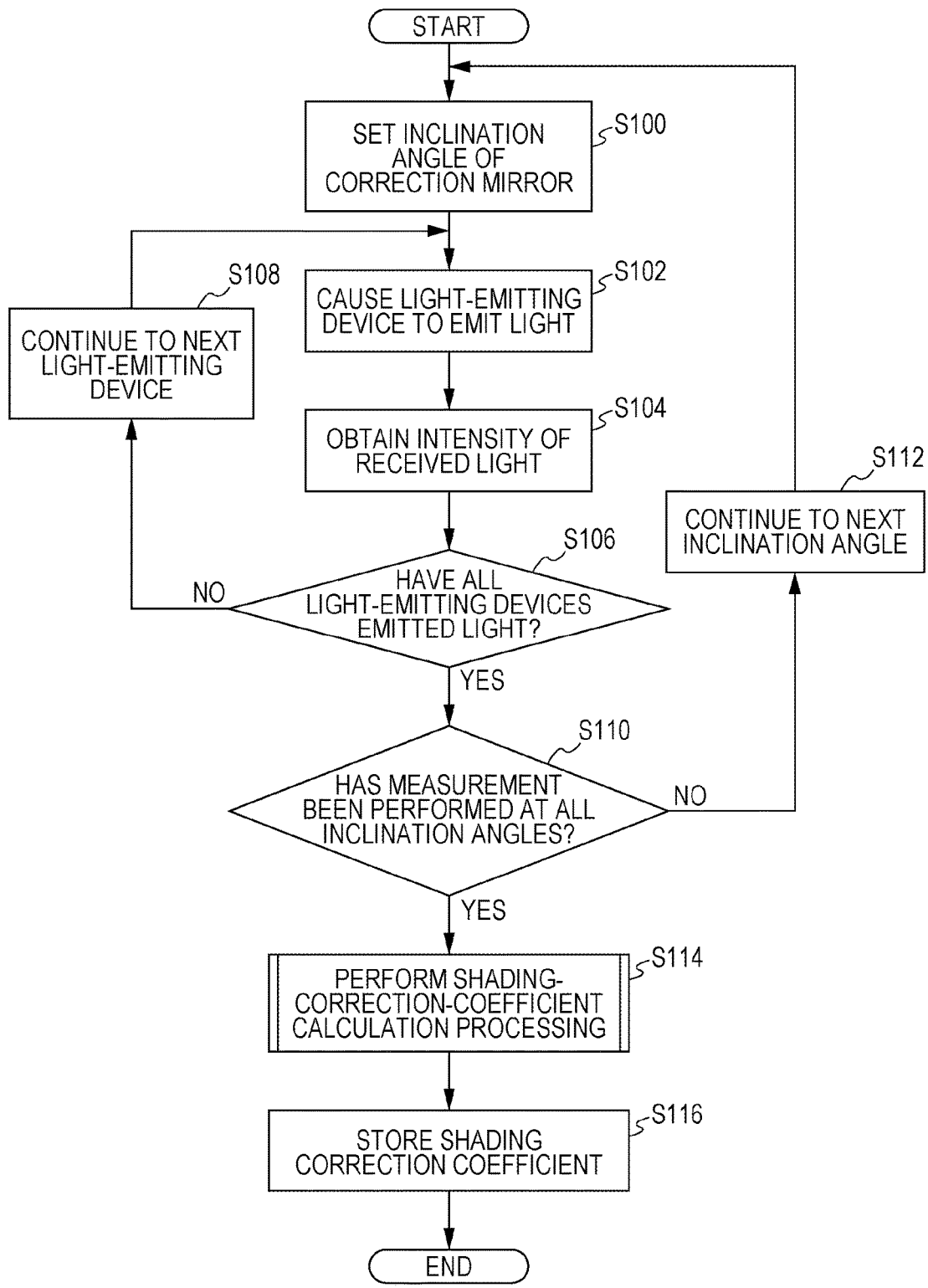

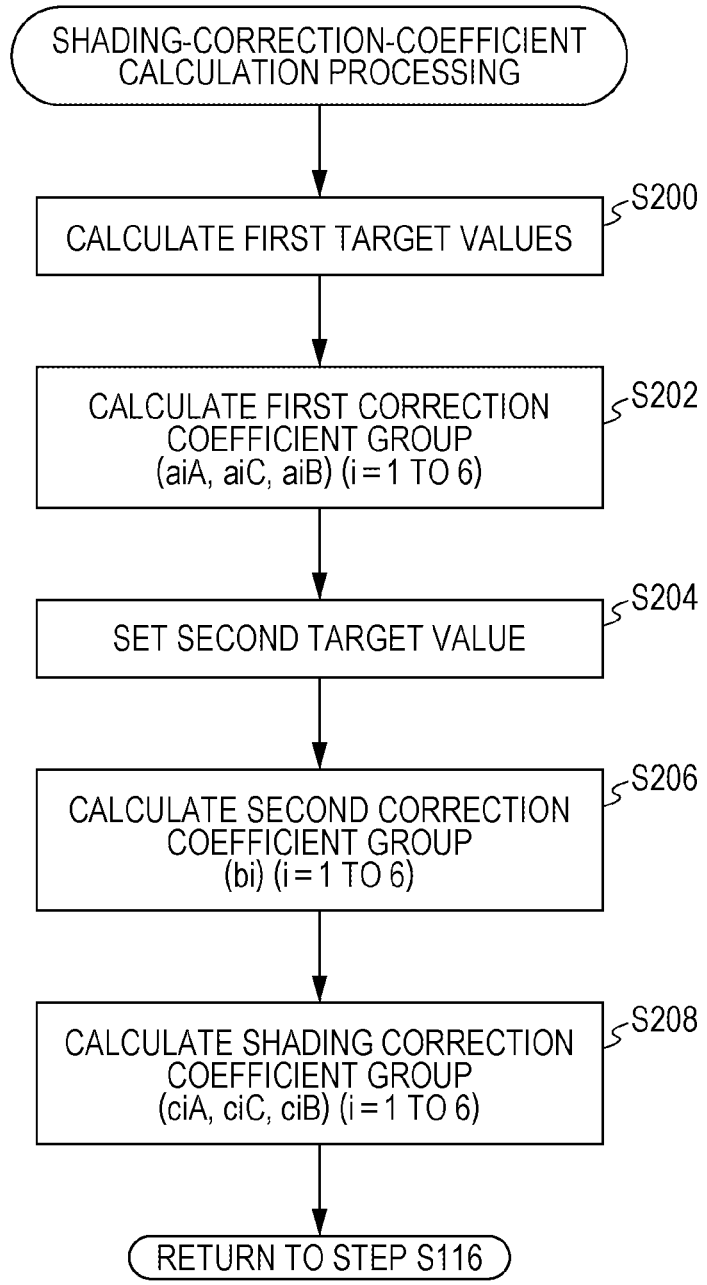

MEASURING DEVICE AND NON-TRANSITORY COMPUTER READABLE MEDIUM

CROSS-REFERENCE TO RELATED APPLICATIONS

This application is based on and claims priority under 35 USC 119 from Japanese Patent Application No. 2015-159804 filed Aug. 13, 2015.

BACKGROUND

Technical Field

The present invention relates to a measuring device and a non-transitory computer readable medium.

SUMMARY

According to an aspect of the invention, there is provided a measuring device including a light-emitting unit that emits irradiation light rays to be radiated onto an object, a first lens that changes a degree of divergence of each of the irradiation light rays emitted by the light-emitting unit, a diaphragm having an aperture that reduces a diameter of each of the irradiation light rays emitted from the first lens, a second lens that converges each of the irradiation light rays, which have passed through the aperture, and radiates the irradiation light ray onto the object in a predetermined direction, a light-receiving unit that is disposed between the diaphragm and the second lens and that receives at least part of reflected light rays corresponding to the irradiation light rays that have been radiated onto and reflected by the object and that have passed through the second lens, a measuring unit that measures the object by using light-receiving results related to the light-receiving unit, a reflector that is disposed as a replacement for the object and whose inclination angle with respect to the irradiation light rays emitted from the second lens is adjustable, and a correction unit that causes the irradiation light rays to be received by the light-receiving unit at different light-receiving positions by varying the inclination angle of the reflector with respect to the irradiation light rays and that performs correction of amounts of the irradiation light rays emitted by the light-emitting unit and correction of a light-receiving sensitivity of the light-receiving unit by using light-receiving results obtained at the light-receiving positions.

BRIEF DESCRIPTION OF THE DRAWINGS

Exemplary embodiments of the present invention will be described in detail based on the following figures, wherein:

FIGS. 7A to 7C are diagrams illustrating operation of the measuring device according to the first exemplary embodiment;

FIGS. 8A to 8D are diagrams for describing correction of light emitting and light receiving systems of a measuring device according to a comparative example;

FIGS. 9A to 9D are diagrams illustrating the operation of the measuring device according to the first exemplary embodiment when correction of the light emitting and light receiving systems is performed;

FIG. 10 is a flowchart illustrating the flow of processes of a correction-processing program according to the first exemplary embodiment;

FIG. 11 is a flowchart illustrating the flow of processes of a subroutine for shading-correction-coefficient calculation processing according to the first exemplary embodiment.

DETAILED DESCRIPTION

First Exemplary Embodiment

Figure 1:
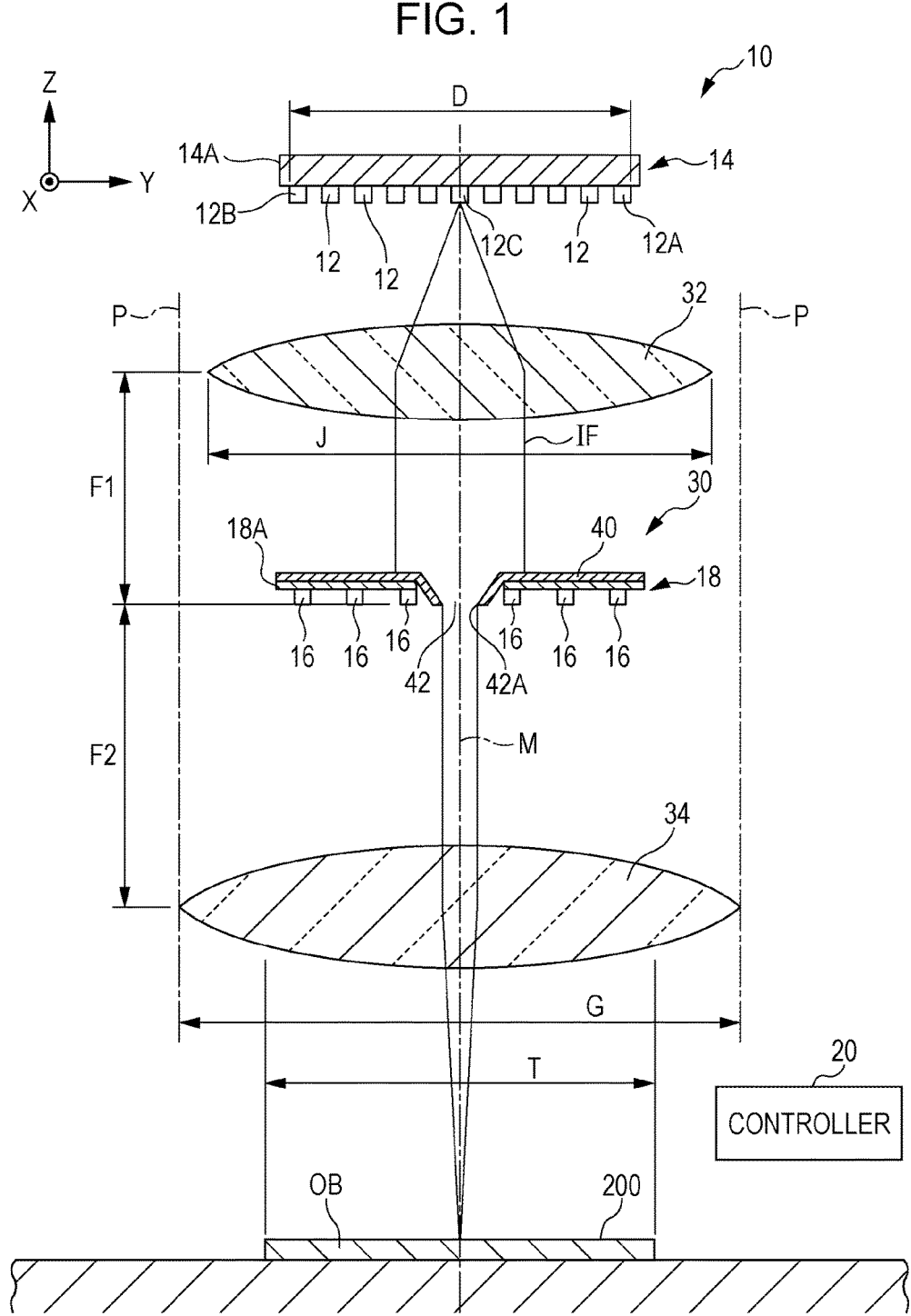
FIG. 1 is a diagram illustrating a configuration of a measuring device according to a first exemplary embodiment of the present invention when the measuring device measures an object.
Figure 2:
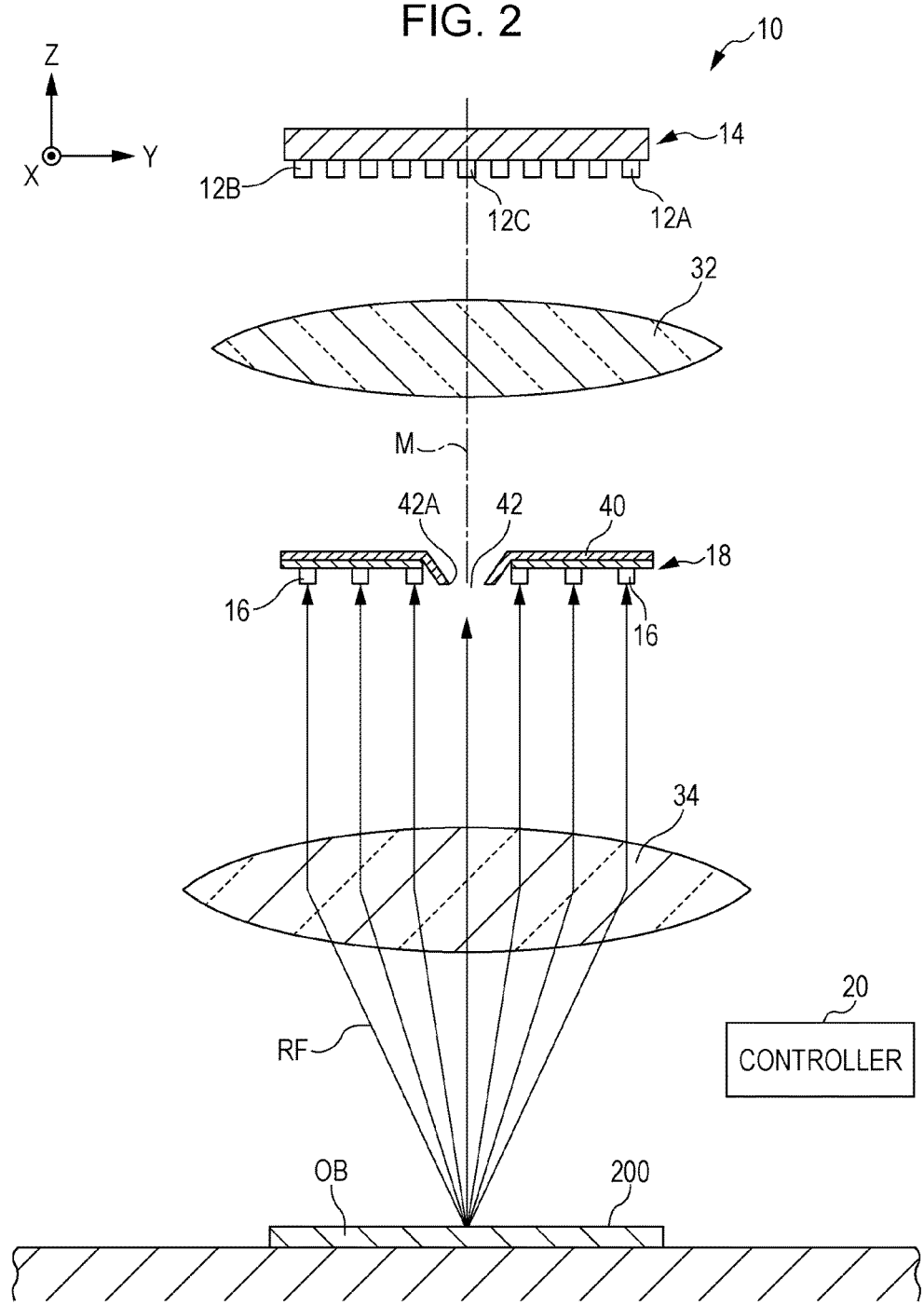
FIG. 2 is a diagram illustrating reflected light rays when the measuring device according to the first exemplary embodiment measures the object.
Figure 3:
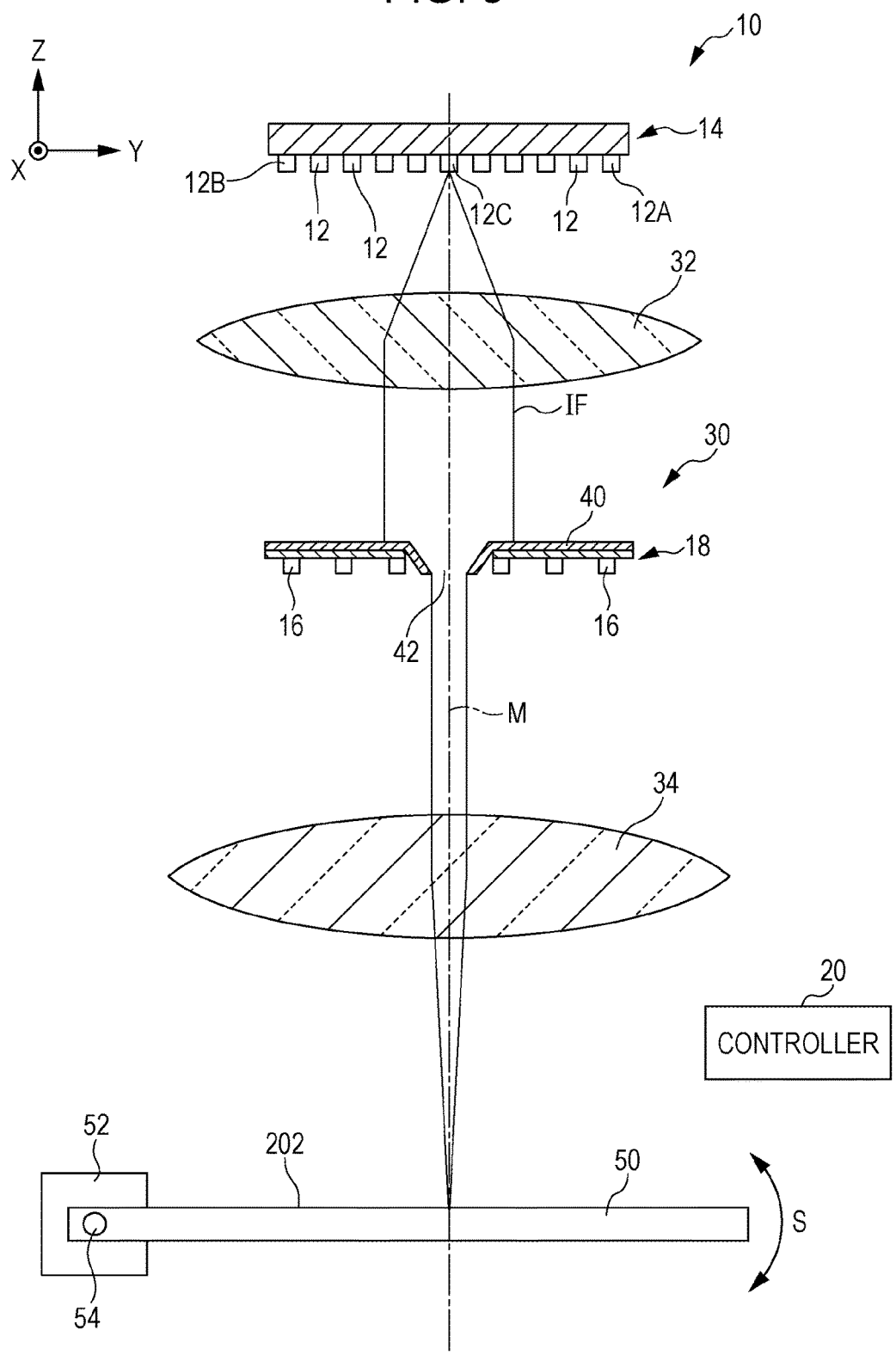
FIG. 3 is a diagram illustrating another configuration of the measuring device according to the first exemplary embodiment when correction of light emitting and light receiving systems is performed.

A first exemplary embodiment of the present invention will be described in detail with reference to FIG. 1 to FIG. 11. First, exemplary configurations of a measuring device 10 according to the first exemplary embodiment will be described with reference to FIG. 1 to FIG. 3. FIG. 1 and FIG. 2 illustrate the configuration of the measuring device 10 when the measuring device 10 measures an object, and FIG. 3 illustrates the configuration of the measuring device 10 when correction of light emitting and light receiving systems of the measuring device 10 is performed.

As illustrated in FIG. 1, the measuring device 10 includes a light-emitting unit 14, an optical system 30, a light-receiving unit 18, and a controller 20. The measuring device 10 sequentially radiates, in a Z-axis direction, light rays onto minute regions of an object OB, which moves in a negative X-axis direction, and obtains a reflection-angle distribution (the reflection-angle dependence of a light-amount distribution) of reflected light rays, which are the irradiation light rays that have been reflected. By using the obtained reflection-angle distribution, changes in the shape of the object OB and surface states (graining, embossing, surface roughness, surface defect, adhesion of foreign matters, and the like) of the object OB are measured without being affected by variations in the distance between the measuring device 10 and in the object OB and the angle of the object OB.

More specifically, as illustrated in FIG. 1, in a top-bottom direction of the measuring device 10 (Z-axis direction), the light-emitting unit 14 is disposed above a measurement region T through which the object OB, which moves in the negative X-axis direction, passes. In addition, the light-emitting unit 14 includes plural light-emitting devices 12 that are mounted in a row on a substrate 14A in a Y-axis direction and whose light-emitting direction is parallel to a negative Z-axis direction. In other words, the plural light-emitting devices 12 are arranged in a direction perpendicular to (crossing) a moving direction (negative X-axis direction)

of the object OB. Note that, in FIG. 1, the light-emitting device 12 that is disposed on an end portion (right end portion in FIG. 1) of the substrate 14A in the Y-axis direction is referred to as a light-emitting device 12A. The light-emitting device 12 that is disposed on the other end portion (left end portion in FIG. 1) of the substrate 14A in the Y-axis direction is referred to as a light-emitting device 12B, and the light-emitting device 12 that is disposed on a center portion of the substrate 14A is referred to as a light-emitting device 12C.

The plural light-emitting devices 12 according to the first exemplary embodiment are configured to emit light rays in such a manner that the light rays are sequentially emitted by the light-emitting devices 12A to 12B at different times, and the light rays emitted by the light-emitting devices 12 are sequentially radiated onto different positions on the object OB. When the object OB is moving in the negative X-axis direction in the measurement region T, one period of light emission performed by the light-emitting devices 12 starting from the light-emitting device 12A to the light-emitting device 12B is repeated several times. FIG. 1 illustrates a pencil of irradiation light rays IF when the light-emitting device 12C emits the irradiation light rays IF, and FIG. 2 illustrates a pencil of reflected light rays RF when the irradiation light rays IF emitted by the light-emitting device 12C has been reflected by a surface 200 of the object OB.

The light-emitting devices 12 are not particularly limited, and as an example, vertical cavity surface emitting lasers (VCSELs), light emitting diodes (LEDs), and the like may be used as the light-emitting devices 12.

The optical system 30 is a so-called double telecentric lens and includes a lens 32, a lens 34, and a diaphragm 40 that is disposed between the lens 32 and the lens 34. The optical system 30 is disposed between the light-emitting unit 14 and the object OB. The optical system 30 guides irradiation light emitted by the light-emitting devices 12 to the object OB and guides reflected light, which is the irradiation light that has been reflected by the object OB, to the light-receiving unit 18. In other words, the light-receiving unit 18 receives at least part of a pencil of light rays that is obtained as a result of the light rays, which have been radiated by the light-emitting device 12 and emitted from the lens 34, being reflected by the object OB and passing through the lens 34 again. In the first exemplary embodiment, an optical axis of the lens 32 and an optical axis of the lens 34 are the same optical axis M, and the optical axis M passes through the center of the light-emitting device 12C of the light-emitting unit 14 and the center of an aperture 42, which will be described later.

As an example, the lens 32 is a convex lens having a circular shape in plan view, and a diameter J of the lens 32 is set to be larger than a dimension D from the light-emitting device 12A to the light-emitting device 12B in the Y-axis direction. Thus, almost all of the light rays emitted by the light-emitting devices 12 pass through the lens 32, and the degree of divergence of the light rays, which have passed through the lens 32, is changed so that the light rays are caused to radiate toward the lens 34 as collimated light rays.

As an example, the lens 34 is a convex lens having a circular shape in plan view, and in the first exemplary embodiment, a diameter G of the lens 34 is set to be larger than the diameter J of the lens 32. In addition, the lens 34 converges a pencil of light rays that is emitted from the lens 32 and that passes through the lens 34 on the surface 200 of the object OB. Note that the position of a light-converging point (focal point) of the lens 34 is not necessarily the same as the position of the surface 200 of the object OB. The position of the light-converging point may be displaced (defocused) from the position of the surface 200 in such a manner as to adjust the irradiation diameters of the irradiation light rays IF on the surface 200, that is, the sizes of to-be-irradiated regions of the object OB. Note that, as an example, each of the irradiation diameters according to the first exemplary embodiment is a few tens of μm.

The diaphragm 40 has the circular aperture 42, which has a substantially circular shape, and a pencil of light rays that has been emitted by one of the light-emitting devices 12 and that has passed through the lens 32 so as to be incident on the lens 34 is reduced in diameter by the aperture 42. More specifically, a plate surface of the diaphragm 40 is formed in a plate shape parallel to an XY plane, and the diaphragm 40 includes an end portion that is tapered by being bent toward the side on which the lens 34 is disposed in the vicinity of the optical axis M. This end portion serves as an aperture edge 42A defining the aperture 42, and the central axis of a circular shape formed of the aperture 42 is the optical axis M. Note that, as an example, the diameter of the aperture 42 according to the first exemplary embodiment is about 1 mm.

In the Z-axis direction, a distance F1 between the aperture edge 42A and the lens 32 is set to be substantially equal to a focal length f1 of the lens 32, and a distance F2 between the aperture edge 42A and the lens 34 is set to be substantially equal to a focal length f2 of the lens 34.

The optical system 30 according to the first exemplary embodiment, which has the above-described configuration, radiates each of the pencils of light rays sequentially emitted by the light-emitting devices 12 as the irradiation light IF whose diameter has been reduced and that is parallel to the optical axis M onto the object OB regardless of the positions of the light-emitting devices 12 (see FIGS. 7A to 7C). In other words, by causing the light-emitting devices 12 to emit light rays and by causing the light rays to scan, pencils of light rays each having a substantially circular cross section and a reduced small diameter, the pencils of light rays being parallel to one another, are sequentially radiated onto the object OB. In addition, in the measuring device 10 according to the first exemplary embodiment, by positioning the object OB in the vicinity of light-converging points of the pencils of the irradiation light rays IF, the light-converging points being formed by the lens 34, the to-be-irradiated regions of the object OB, onto which the irradiation light rays IF are to be radiated, are formed so as to be minute regions whose diameters are substantially equal to one another.

The light-receiving unit 18 includes plural light-receiving devices 16 and receives the reflected light rays RF that are light rays that have been reflected by the object OB and that have passed through the lens 34 of the optical system 30. The light-receiving unit 18 according to the first exemplary embodiment is disposed below the diaphragm 40, which is disposed between the lens 32 and the lens 34, in the Z-axis direction. The light-receiving devices 16 are not particularly limited, and for example, photodiodes (PDs), charge coupled devices (CCDs), and the like may be used as the light-receiving devices 16.

Since the light-receiving unit 18 is disposed between the lens 32 and the lens 34, the light-receiving devices 16 are also disposed between the lens 32 and the lens 34. Here, the term "the light-receiving devices 16 are disposed between the lens 32 and the lens 34" refers to the case where light-receiving devices 16 are disposed within a cylindrical surface formed of lines P each of which extends in the Z-axis direction and passes through an outer diameter edge of the lens 34 (an imaginary contact point of a front surface radius (R) and a rear surface R) as illustrated in FIG. 1.

Figure 4A:
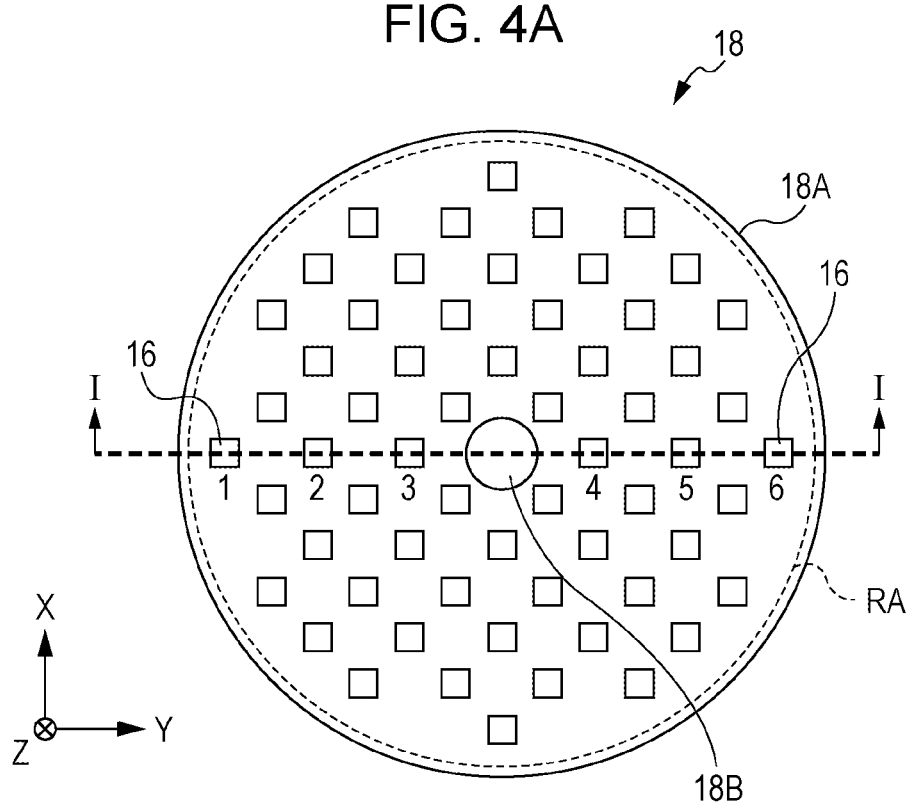
FIG. 4A is a plan view illustrating an exemplary configuration of a light-receiving unit according to the first exemplary embodiment.

FIG. 4A illustrates an exemplary configuration of the light-receiving unit 18. FIG. 4A is a plan view of the light-receiving unit 18 as seen from the Z-axis direction. FIG. 1 is a sectional view of the light-receiving unit 18 taken along line I-I of FIG. 4A. As illustrated in FIG. 4A, as an example, in the light-receiving unit 18, the plural light-receiving devices 16 are arranged in a planar form (arranged in an array) on a substantially circular substrate 18A having a substantially circular aperture 18B formed at the center of the substrate 18A. FIG. 4A illustrates the case where 60 light-receiving devices 16 are provided. In the measuring device 10, all of the plural light-receiving devices 16 serve as a light-receiving region RA that receives the reflected light RF. Note that, although the light-receiving unit 18 in which the plural light-receiving devices 16 are arranged on the entire surface of the substrate 18A is illustrated in FIG. 4A as an example, the light-receiving unit 18 is not limited to this configuration, and the light-receiving unit 18 may have a configuration in which the light-receiving devices 16 are arranged on a portion of the substrate 18A in accordance with the range of the reflected light rays RF to be received.

Figure 4B:
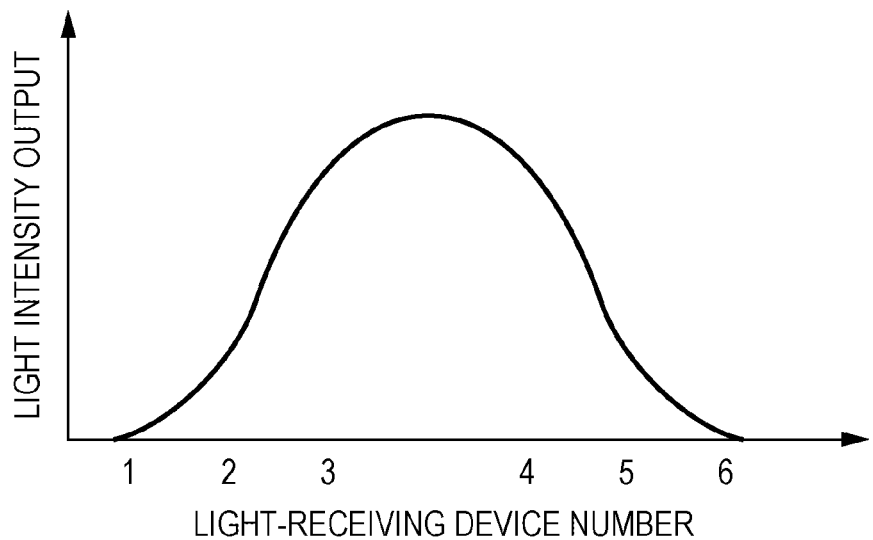
FIG. 4B is a graph.

As an example, the light-receiving region RA receives part of the reflected light rays RF at an angle in the range of 0 degrees to 40 degrees around an axis that is parallel to the optical axis M. When the light-receiving region RA receives the reflected light rays RF, a three-dimensional distribution is generated in accordance with the amounts of light received by the light-receiving devices 16. In the case where the reflected light rays RF are isotropic as in the case where the reflected light rays RF are reflected by a perfect diffusing surface, the cross-sectional shape of the three-dimensional distribution when the three-dimensional distribution is cut in a plane including the Z-axis is a substantially a Gaussian curve as illustrated in FIG. 4B. Note that light-receiving device numbers 1 to 6 shown on the horizontal axis of FIG. 4B correspond to the numbers 1 to 6 of the light-receiving devices 16 illustrated in FIG. 4A. Since the spaces between the light-receiving devices 16 in the light-receiving region RA do not receive the reflected light rays RF, the actual output distribution is discrete. However, such discreteness is not illustrated in FIG. 4B.

In addition, in the measuring device 10, light-receiving surfaces of the light-receiving devices 16 and the aperture edge 42A are located at the same position in the Z-axis direction, and thus, the distance F2 between the light-receiving surfaces of the light-receiving devices 16 and the lens 34 is equal to the focal length f2 of the lens 34. Therefore, even in the case where the position of the object OB is changed vertically in the Z-axis direction or changed horizontally in the Y-axis direction and where the irradiation light rays IF are radiated from the different light-emitting devices 12, the output distribution in the light-receiving region RA is constant as long as the positions where the irradiation light rays IF are radiated onto the object OB do not change.

In other words, when a fine region having a size substantially the same as that of the irradiation diameter is assumed as the object OB, in the case where the object OB moves vertically in the Z-axis direction or moves horizontally in the Y-axis direction, the object OB is irradiated with different irradiation light rays IF emitted by the different light-emitting devices 12 and reflects different reflected light rays RF. However, in the measuring device 10 according to the first exemplary embodiment, the output distribution generated by all of the plural light-receiving devices 16 included in the light-receiving region RA is constant regardless of the positions where the reflected light rays RF are generated.

Figure 5:
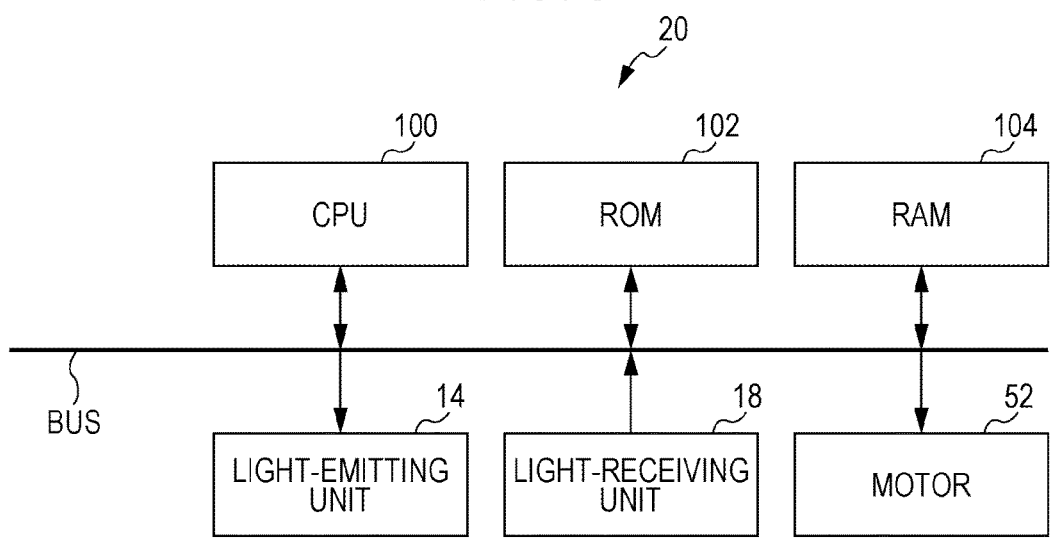
FIG. 5 is a block diagram illustrating an exemplary configuration of a controller according to the first exemplary embodiment.

As illustrated in FIG. 5, the controller 20 includes a central processing unit (CPU) 100, a read only memory (ROM) 102, and a random access memory (RAM) 104. The CPU 100 integrally controls the overall system of the measuring device 10. The ROM 102 is a memory that stores beforehand a control program of the measuring device 10, a correction-processing program (described later), and the like. The RAM 104 is a memory that is used as a work area or the like when running a program, such as the control program. The CPU 100, the ROM 102, and the RAM 104 are connected to one another via a bus.

The light-emitting unit 14, the light-receiving unit 18, and a motor 52 that drives a correction mirror 50, which will be described later, are connected to the bus, and the light-emitting unit 14, the light-receiving unit 18, and the motor 52 are controlled by the CPU 100 via the bus.

Figure 6A:
FIGS. 6A to 6C are time charts for describing control of a light-emitting unit and the light-receiving unit according to the first exemplary embodiment.
Figure 6B:
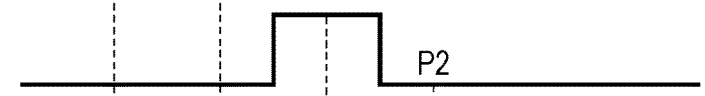
Figure 6C:
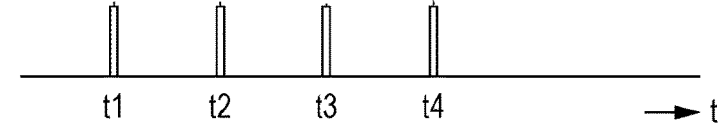

Control of the light-emitting unit 14 and the light-receiving unit 18 performed by the controller 20 will now be described with reference to FIGS. 6A to 6C. FIG. 6A and FIG. 6B respectively illustrate a light-emitting pulse signal P1 that is used for causing one of the light-emitting devices 12 to emit light and a light-emitting pulse signal P2 that is used for causing the next one of the light-emitting devices 12 to emit light in the case where the light-emitting devices 12 of the light-emitting unit 14 are caused to sequentially emit light as described above. As illustrated in FIGS. 6A and 6B, in the control of the light-emitting unit 14 according to the first exemplary embodiment, a predetermined period of time over which there is no signal (zero level) is set between the light-emitting pulse signal P1 and the light-emitting pulse signal P2 (portions corresponding to time t2 and time t4 in FIGS. 6A and 6B). FIG. 6C illustrates reading pulses that are generated when the light-receiving unit 18 receives the reflected light rays RF corresponding to the irradiation light rays IF that have been generated by the light-emitting devices 12 as a result of the light-emitting pulse signals P1 and P2 and that have been reflected. The amounts of light received by all the light-receiving devices 16, which are included in the light-receiving unit 18 (i.e., the light-receiving devices 16 in the light-receiving region RA), are read by using the reading pulses, and signals representing the output distribution are generated.

First, the reflected light RF corresponding to the irradiation light IF generated by the light-emitting pulse signal P1 is read by all of the light-receiving devices 16 at time t1. In this case, when there are k light-receiving devices 16, k light-receiving signals $Sr(1)$, $Sr(2)$, . . . , $Sr(k)$ are obtained from the light-receiving devices 16. Next, a received light amount at zero level between the light-emitting pulse signal P1 and the light-emitting pulse signal P2 is read by all of the light-receiving devices 16 at time t2. Here, k light-receiving signals at zero level that have been read by all of the light-receiving devices 16 are $Sr0(1)$, $Sr0(2)$, . . . , $Sr0(k)$. Next, difference values between the light-receiving signals of the reflected light RF and the light-receiving signals at zero level, which have been obtained by all of the light-receiving devices 16, that is, $Sr(1)-Sr0(1)$, $Sr(2)-Sr0(2)$, . . . , $Sr(k)-Sr0(k)$ are calculated, and these k difference values form the output distribution of received light amount. Also in the case of each of the light-emitting pulse signal P2 and the subsequent light-emitting pulse signals, an output distribution is calculated in a similar manner to the above. The calculated output distributions may be temporarily stored in a memory such as the RAM 104.

Note that, as described above, the signals representing the output distribution of the reflected light RF are generated by subtracting the light-receiving signals obtained when there is no signal from the light-receiving signals of the reflected light RF in order to eliminate the influence of ambient light. Accordingly, in the case where the influence of ambient light is negligible, the light-receiving signals of the reflected light RF may be used as they are as the signals representing the output distribution. In addition, in this case, it is not necessary to cause the light-emitting pulse signals that are successive with one another to be spaced apart in time from one another, and since the timing at which the reflected light RF is received is dependent on the reading pulses, portions of the light-emitting pulse signals may be superposed with one another.

The configuration of the measuring device 10 when correction of the light emitting and light receiving systems according to the first exemplary embodiment is performed will now be described with reference to FIG. 3. As illustrated in FIG. 3, in the case of performing correction of the amount of light emitted by each of the light-emitting devices 12, which are included in the light-emitting unit 14 of the measuring device 10, and correction of the light-receiving sensitivity of each of the light-receiving devices 16, which are included in the light-receiving unit 18, (correction of the light emitting and light receiving systems), the correction mirror 50 is disposed instead of the object OB at the position where the object OB would be disposed.

An end of the correction mirror 50 is fixed to a rotary shaft 54 of the motor 52, and the correction mirror 50 is capable of rotating in the direction of arrow S in FIG. 3 as a result of being driven by the motor 52. Although, as an example, a stepping motor whose rotation angle may be minutely set is employed as the motor 52 according to the first exemplary embodiment, the motor 52 is not limited to such a stepping motor, and a different type of motor may be used in accordance with the precision of a set angle and the like. Note that, in FIG. 3, although the configuration in which the motor 52 is positioned at the left end of the correction mirror 50 as viewed in FIG. 3 is illustrated as an example, it is obvious that the present invention is not limited to this configuration, and the motor 52 may be positioned at the right end of the correction mirror 50 as viewed in FIG. 3 or may be positioned at the center of the correction mirror 50. Note that details of correction of the light emitting and light receiving systems using the correction mirror 50 will be described later.

Operation of the measuring device 10 when the measuring device 10 measures a reflection characteristic (e.g., degree of surface irregularities) of the object OB will now be described with reference to FIGS. 7A to 7C. FIGS. 7A to 7C illustrate pencils of the irradiation light rays IF when the light-emitting devices 12A, 12C, and 12B of the light-emitting unit 14 sequentially emit light and pencils of the reflected light rays RF which are the pencils of the irradiation light rays IF that have been reflected by the surface 200 of the object OB and guided to the light-receiving unit 18.

First, when a leading end of the object OB has entered in the measurement region T as a result of the object OB moving in the negative X-axis direction, the light-emitting devices 12 sequentially emit the irradiation light rays IF at different times, and the irradiation light rays IF are sequentially radiated onto the object OB. Then, one period of light emission performed by the light-emitting devices 12 starting from the light-emitting device 12A to the light-emitting device 12B is repeated until a trailing end of the object OB passes through the measurement region T. As described above, the light emission performed by each of the light-emitting devices 12 is controlled by the controller 20.

The degree of divergence of each of the pencils of irradiation light rays IF emitted by the light-emitting devices 12 is changed by the lens 32 in such a manner that the pencil of irradiation light rays IF is oriented in a direction toward the lens 34. Each of the pencils of irradiation light rays IF whose degree of divergence has been changed by the lens 32 is reduced (limited) in diameter by the diaphragm 40. Each of the pencils of irradiation light rays IF that has been reduced in diameter by the diaphragm 40 is converged by the lens 34 and radiated onto the object OB in the Z-axis direction (direction parallel to the optical axis M). In other words, the object OB is disposed in the vicinity of light-converging points to which the irradiation light rays IF are converged by the lens 34. As described above, as an example, each of the irradiation light rays IF according to the first exemplary embodiment is converged on the surface 200 of the object OB in such a manner that the irradiation diameter thereof is a few tens of μm.

The irradiation light rays IF, which are radiated onto the object OB, are reflected by the surface 200 of the object OB, and as a result, the reflected light rays RF (indicated by dashed arrows in FIGS. 7A to 7C) are generated. The orientation of each of the pencils of the reflected light rays RF is changed by the lens 34 in such a manner that the pencil of the reflected light rays RF radiates in a direction toward the light-receiving devices 16. The reflected light rays RF that have passed through the lens 34 are received by the light-receiving devices 16.

Although the irradiation light rays IF are reflected in various directions in accordance with the state of the surface 200 of the object OB, in the first exemplary embodiment, as described above, part of the reflected light rays RF at angles in the range of 0 degrees to 40 degrees around an axis that passes through an incident point at which the irradiation light IF is incident on the surface 200 and that is parallel to the optical axis M is received. Thus, the light-receiving region RA of the light-receiving unit 18 corresponding to the irradiation light IF emitted by one of the light-emitting devices 12 has a substantially circular shape. An example of the light-receiving region RA is illustrated in FIG. 4A.

As described above, the light-receiving signals obtained by the light-receiving devices 16 are read at a predetermined timing in response to control by the controller 20. The light-receiving signals, which have been read, may be temporarily stored in a memory such as the RAM 104. The controller 20 generates an output distribution (light-receiving profile) in the light-receiving region RA by using the light-receiving signals (luminance signals) each corresponding to one of the light-emitting devices 12. Since this output distribution includes information regarding the angles of the reflected light rays RF, for example, the degree of surface irregularities of the object OB is measured.

Before describing the correction of the light emitting and light receiving systems according to the first exemplary embodiment with reference to FIG. 9A to FIG. 11, correction of light emitting and light receiving systems according to a comparative example will now be described with reference to FIGS. 8A to 8D. FIGS. 8A to 8C illustrate operation of a measuring device 90 according to the comparative example when the correction of the light emitting and light receiving systems is performed. In the correction of the light emitting and light receiving systems illustrated in FIGS. 8A to 8C, a method for correcting the amounts of light emitted by light-emitting devices and the sensitivities of light-receiving devices at the same time is used.

As illustrated in FIG. 8A to 8C, like the measuring device 10, the measuring device 90 includes the light-emitting unit 14 including the plural light-emitting devices 12, the lenses 32 and 34, the diaphragm 40, and the light-receiving unit 18 including the plural light-receiving devices 16. The light-emitting unit 14, the lenses 32 and 34, the diaphragm 40, and the light-receiving unit 18 have functions the same as those in the measuring device 10, and thus, descriptions thereof will be omitted. In the case of performing correction of the light emitting and light receiving systems, the measuring device 90 further includes a reference sample DS formed from a perfect diffusing material.

The perfect diffusing material is a material having a perfect diffusing surface, that is, a surface in which the intensity distribution of reflected light is not dependent on the direction of incident light and is proportional to a solid angle at which a reflecting surface is viewed. Therefore, reflected light within a fixed solid angle at which the reflecting surface is viewed may be obtained from the irradiation light IF emitted by each of the light-emitting devices 12, and thus, the irradiation light IF emitted by each of the light-emitting devices 12 may be reflected by a surface of the reference sample DS and received by all of the light-receiving devices 16 at the same time.

FIGS. 8A to 8C illustrate pencils of the irradiation light rays IF when the light-emitting devices 12A, 12C, and 12B are caused to sequentially emit light and pencils of the reflected light rays RF which are the irradiation light rays IF that have been reflected by the surface of the reference sample DS. In each of FIGS. 8A to 8C, only one light ray at the center of the pencil of the irradiation light rays IF is illustrated.

In each of FIGS. 8A to 8C, a characteristic of the surface of the reference sample DS causes the irradiation light rays IF to be isotropically reflected with substantially the same reflectance at the incident points of the irradiation light rays IF, and as a result, the reflected light rays RF are received by the light-receiving devices 16. Accordingly, by causing the light-emitting devices 12 to sequentially emit light and by radiating the irradiation light rays IF, which are parallel to the optical axis M, onto the reference sample DS, the reflected light rays RF each corresponding to one of the light-emitting devices 12 are guided to the light-receiving devices 16, and the amounts of light received by all of the light-receiving devices 16 are measured in response to control by the controller 20.

FIG. 8D illustrates output distributions (received light amount distributions) in the light-receiving unit 18 when each of the light-emitting devices 12A, 12C, and 12B emits light. Since the reflecting surface by which the irradiation light rays IF are reflected is the surface of the reference sample DS that is close to a perfect diffusing surface, the output distributions illustrated in FIG. 8D, each of which corresponds to one of the light-emitting devices 12, each approximate to a Gaussian curve. On the basis of the output distributions each corresponding to one of the light-emitting devices 12, for example, the peak values of the output distributions are obtained, and correction coefficients for the output distributions that are used for adjusting a predetermined reference, which is, for example, a maximum value of the peak values, are calculated.

In the subsequent measurement, shading correction is performed by multiplying received-light outputs of the light-receiving unit 18 each corresponding to one of the light-emitting devices 12 by the corresponding correction coefficients. In the above-described manner, the correction of the light emitting and light receiving systems according to the comparative example is performed. According to the method of correcting the light emitting and light receiving systems of the comparative example, each of the irradiation light rays IF of the light-emitting devices 12 is guided to the light-receiving devices 16 at the same time, and thus, the correction of the light emitting and light receiving systems may be relatively easily performed.

However, a reflection-angle distribution in the perfect diffusing material is not uniform even though the reflectance of the perfect diffusing material is approximately uniform. In addition, although it may be said that the reflectance is uniform with respect to an irradiation light ray having a diameter of a few mm that is used in a common measuring device, the reflectance is no longer uniform with respect to an irradiation light ray having a diameter of a few tens of μm such as that used in the measuring device 10 according to the first exemplary embodiment because the irradiation spot area of the irradiation light ray whose diameter is a few tens of μm is of an order of magnitude about 10,000 times smaller than that of the irradiation spot area of the irradiation light ray whose diameter is a few mm. Therefore, it may sometimes be required to devise a better method depending on a measurement precision required for a measuring device.

Meanwhile, the following method is a conceivable example of a method of individually performing correction of variations in the amounts of light rays emitted by the light-emitting devices 12 (correction of the light emitting system) and correction of variations in the sensitivities of the light-receiving devices 16 (correction of the light receiving system).

That is to say, in the correction of the light emitting system, a light-amount measuring device that is capable of moving in the Y-axis direction (see FIG. 1) is provided in such a manner as to be positioned where the incident points at which the irradiation light rays IF are incident on the object OB are formed in the measuring device 10. Then, the light-emitting devices 12 are caused to sequentially emit the irradiation light rays IF in such a manner that the irradiation light rays IF sequentially radiate in a direction parallel to the optical axis M of the optical system, and the amounts of the irradiation light rays IF emitted by the light-emitting devices 12 are measured while moving the light-amount measuring device in the Y-axis direction. Another conceivable example is a method of collectively measuring the amounts of the irradiation light rays IF emitted by all of the light-emitting devices 12 by using a light-amount measuring device that has a uniform sensitivity in an area including, in plan view, regions irradiated with the irradiation light rays IF emitted by all of the light-emitting devices 12. However, in the case of using the first-described method, the measuring device 10 becomes complex. Using the second-described method leads to an increase in the manufacturing costs of the light-amount measuring device, and a light-receiving circuit becomes complex.

Meanwhile, in the correction of the light receiving system, a light source for use in correction is provided in such a manner as to be positioned at the incident points at which the irradiation light rays IF are incident on the object OB in the measuring device 10. The light source for use in correction is capable of moving in the Y-axis direction (see FIG. 1) and emits light having a reference amount while the light radiation angle of the light source is adjustable in a yz plane. Then, the sensitivity of each of the light-receiving devices 16 is measured by causing all of the light-receiving devices 16 to receive the light emitted by the light source for use in correction while varying the light radiation angle of the light source. However, in this method, a mechanism for moving the light source for use in correction and a mechanism for adjusting the light radiation angle are required, and as a result, the measuring device 10 becomes complex.

The number of processes in a method of correcting variations in the amounts of light rays emitted by the light-emitting devices 12 and variations in the sensitivities of the light-receiving devices 16 at the same time as in the case of the correction of the light emitting and light receiving systems according to the above-described comparative example is smaller than the number of processes in a method of individually correcting the light emitting system and the light receiving system as described above.

Accordingly, as illustrated in FIG. 3, the measuring device 10 according to the first exemplary embodiment includes the correction mirror 50 that is used for correcting the light emitting and light receiving systems, and the light emitting system and the light receiving system undergo the shading correction at the same time. The correction mirror 50 according to the first exemplary embodiment is a total reflection mirror having a surface 202 that specularly reflects light, and for example, a mirror formed of a glass or a metal coated with a metal thin film is used as the correction mirror 50. It is obvious that the correction mirror 50 is not limited to such a total reflection mirror and may be a semi-transmissive mirror or may be a mirror having a different structure.

Correction of the light emitting and light receiving systems according to the first exemplary embodiment will now be described with reference to FIGS. 9A to 9D. FIGS. 9A to 9C illustrate pencils of the irradiation light rays IF when the light-emitting devices 12A, 12C, and 12B emit light and pencils of the reflected light rays RF which are the pencils of the irradiation light rays IF that have been reflected by the correction mirror 50 inclined at a predetermined inclination angle θ. As illustrated in FIGS. 9A to 9C, in the first exemplary embodiment, causing each of the light-emitting devices 12A, 12C, and 12B to emit light corresponds to changing the positions of the irradiation light rays IF, which are parallel to the optical axis M and that are radiated onto the object OB, that is, changing the positions of the reflected light rays RF.

In each of FIGS. 9A to 9C, only one light ray at the center of the pencil of the irradiation light rays IF is illustrated. Since the correction mirror 50 according to the first exemplary embodiment specularly reflects light, each of the pencils of the reflected light rays RF is extremely thin (illustrated as one light ray in each of FIGS. 9A to 9C). Accordingly, in the following description, each of the reflected light rays RF, which correspond to the irradiation light rays IF from the light-emitting devices 12, is received by one of the light-receiving devices 16 (i.e., each of the reflected light rays RF will not be received by more than one of the light-receiving devices 16 at the same time).

In correction of the light emitting and light receiving systems according to the first exemplary embodiment, the light-emitting devices 12 are caused to sequentially emit light in a state where the inclination angle θ of the correction mirror 50 is set to a fixed angle, and the amounts of the reflected light rays RF, which correspond to the light rays emitted by the light-emitting devices 12, received by one of the light-receiving devices 16 are measured. This measurement is repeated by varying the inclination angle θ of the correction mirror 50 so as to cause the light-receiving devices 16 to sequentially receive the reflected light rays RF, and measured values, which are obtained by combining light emission performed by all of the light-emitting devices 12 and light reception performed by all of the light-receiving devices 16, are obtained. By using these measured values, shading correction coefficients each of which is used for one of the combinations of the light-emitting devices 12 and the light-receiving devices 16 are calculated, and the correction of the light emitting and light receiving systems is performed.

Here, as illustrated in FIG. 4A, the light-receiving unit 18 according to the first exemplary embodiment includes the light-receiving devices 16, which are arranged in a planar form, and thus, it is necessary to cause the irradiation light rays IF, which are emitted by the light-emitting devices 12 and which are incident on the light-receiving devices 16, to scan two-dimensionally. However, in order to simplify the drawings, in the following description, the irradiation light rays IF, which are incident on the light-receiving devices 16, are considered to be caused, by the motor 52, to scan one-dimensionally, that is, to scan in the yz plane. Note that, in the case of causing the irradiation light rays IF to scan two-dimensionally, a mechanism, such as a goniostage, that has two rotary shafts and that is capable of inclining may be used instead of the motor 52.

FIG. 9A illustrates the case where the light-emitting device 12A is caused to emit light while the inclination angle θ of the correction mirror 50 is set to an inclination angle θ1 and where the light is received by one of the light-receiving devices 16 whose light-receiving device number is 1 (see FIG. 4A). The light-receiving device 16 whose light-receiving device number is i will hereinafter be referred to as "light-receiving device 16-i". Similarly, FIG. 9B illustrates the case where the light-emitting device 12C is caused to emit light and where the light is received by the light-receiving device 16-1, and FIG. 9C illustrates the case where the light-emitting device 12B is caused to emit light and where the light is received by the light-receiving devices 16-1. In the manner described above, each of the light-emitting devices 12 is caused to emit light in a state where the inclination angle θ of the correction mirror 50 is set to the inclination angle θ1, and the amount of the light emitted by each of the light-emitting devices 12 is measured by using the light-receiving device 16-1. In this manner, in the measuring device 10 according to the first exemplary embodiment, due to the above-described characteristic of the optical system 30, the irradiation light rays IF are received by the same light-receiving device 16 as long as the angle of the reflecting surface with respect to the irradiation light rays IF is a fixed angle.

Next, the inclination angle θ of the correction mirror 50 is set to the inclination angle θ2, and each of the light-emitting devices 12 is caused to emit light in such a manner that the light is received by the light-receiving device 16-2. Then, the amount of the light emitted by each of the light-emitting devices 12 is measured by using the light-receiving device 16-2. This operation is performed on each of the light-receiving devices 16-3, 16-4, 16-5, and 16-6, so that measurement results of light amount outputs illustrated in FIG. 9D are obtained. In the measuring device 10 according to the first exemplary embodiment, correction coefficients used for performing shading correction are calculated by using the measurement results of the light amount outputs illustrated in FIG. 9D, which have been obtained by measuring the amount of light emitted by each of the light-emitting devices 12 in each of the light-receiving devices 16, and the correction of the light emitting and light receiving systems is performed.

Note that, in the measuring device 10 according to the first exemplary embodiment, as described above, the controller 20 controls the timings at which the light-emitting devices 12 emit light and the timings at which light-receiving signals are read by the light-receiving devices 16 and performs control for setting the inclination angle θ of the correction mirror 50.

The correction-processing program for performing correction of the light emitting and light receiving systems according to the first exemplary embodiment will now be described with reference to FIG. 10 and FIG. 11. FIG. 10 is a flowchart illustrating the flow of processes of the correction-processing program according to the first exemplary embodiment, and FIG. 11 is a flowchart illustrating the flow of processes of a subroutine for shading-correction-coefficient calculation processing that is invoked by the correction-processing program. For example, when a user issues a start instruction via an input unit (not illustrated), the correction-processing program is read by the CPU 100 of the controller 20 from a memory such as the ROM 102, and the processes illustrated in FIG. 10 are executed. In the correction-processing program, the inclination angle θ of the correction mirror 50 at which one of the light-receiving devices 16 is caused to receive the irradiation light rays IF from the light-emitting devices 12 is set beforehand and stored in a memory such as the ROM 102.

As illustrated in FIG. 10, in step S100, the inclination angle θ of the correction mirror 50 is set in such a manner that the reflected light RF is received by a first light-receiving device 16. In other words, the motor 52 is controlled in such a manner that the inclination angle of the correction mirror 50 is set to a predetermined angle θ. In the case where values of the inclination angle θ each corresponding to one of the light-receiving devices 16 are stored beforehand in a memory such as the ROM 102, the motor 52 is controlled while reading the corresponding inclination angle θ from the ROM 102 or the like.

In the next step S102, the first light-emitting device 12 is caused to emit light.

In the next step S104, the amount of light received by the light-receiving device 16, which has been set in step S100, is measured, and the measured value is obtained. The received-light amount, which has been obtained, may be temporarily stored in a memory such as the RAM 104.

In the next step S106, it is determined whether all of the light-emitting devices 12 have emitted light. In the case where the determination result is No, the next light-emitting device 12 is set to emit light in step S108. Then, the process returns to step S102, and light emission is continued by the next light-emitting device 12. On the other hand, in the case where the determination result is Yes, the process proceeds to step S110.

In step S110, it is determined whether the above measurement has been performed at all of the inclination angles, that is, the above measurement has been performed on all of the light-receiving devices 16. In the case where the determination result is No, preparation for the measurement at the next inclination angle is performed in step S112, and then the process returns to step S100 so as to continue the setting of the inclination angle of the correction mirror 50. On the other hand, in the case where the determination result is Yes, the process proceeds to step S114.

In step S114, the subroutine for shading-correction-coefficient calculation processing is invoked, the subroutine for shading-correction-coefficient calculation processing being used for calculating coefficients for use in the shading correction by using the measured values of the light amount outputs such as those illustrated in FIG. 9D, which have been obtained beforehand.

In the next step S116, the shading correction coefficients, which have been calculated in step S114, are stored in a memory such as the RAM 104 or a non-volatile memory (NVM), which is not illustrated, for the subsequent shading correction. After that, the correction-processing program is exited.

The subroutine for shading-correction-coefficient calculation processing will now be described with reference to FIG. 11. The shading correction coefficients in the first exemplary embodiment are coefficients by each of which measured values of the light amount outputs of the light-emitting devices 12 in each of the light-receiving devices 16, such as those illustrated in FIG. 9D, are multiplied in order to adjust the measured values to a single value, that is, in order to adjust 18 measured values illustrated in FIG. 9D to a single value.

First, when the determination result in step S110 of the above-described correction-processing program is Yes, the following measured values are stored in a memory such as the RAM 104. In other words, when the light amount outputs of the light-emitting device 12A, the light-emitting device 12C, and the light-emitting device 12B measured in the light-receiving device 16-$i$ are referred to as ViA, ViC, and ViB, respectively, the following 18 measured values are stored.

In light-receiving device 16-1, (V1A, V1C, V1B)
In light-receiving device 16-2, (V2A, V2C, V2B)
In light-receiving device 16-3, (V3A, V3C, V3B)
In light-receiving device 16-4, (V4A, V4C, V4B)
In light-receiving device 16-5, (V5A, V5C, V5B)
In light-receiving device 16-6, (V6A, V6C, V6B)

Among the above measured values, the measured values in the light-receiving device 16-3 are illustrated in FIG. 9D.

First, in step S200, first target values are calculated. Each of the first target values is a representative value for the light-receiving device 16-$i$ used for adjusting the light amount outputs (ViA, ViC, and ViB) of the light-emitting devices 12, which are measured in the light-receiving device 16-$i$, to a single value. In a method of calculating the first target values, any one of a maximum value, a minimum value, an average value, a median value, and the like, may be used, and a maximum value is used in the first exemplary embodiment.

In this case, when the maximum value among the light amount outputs (ViA, ViC, and ViB) is referred to as Vim, referring to the measurement results illustrated in FIG. 9D, the first target values corresponding to the light-receiving devices 16 are as follows.

In light-receiving device 16-1, (V1m=V1C)
In light-receiving device 16-2, (V2m=V2C)
In light-receiving device 16-3, (V3m=V3C)
In light-receiving device 16-4, (V4m=V4C)
In light-receiving device 16-5, (V5m=V5C)
In light-receiving device 16-6, (V6m=V6C)

Note that, in the case of using another method of calculating the first target values, which is, for example, a method using an average value, when the average value of the measured values in the light-receiving device 16-$i$ is referred to as Via, the first target value may be Via=(ViA+ViC+ViB)/3.

In the next step S202, a first correction coefficient group (aiA, aiC, aiB) (i=1 to 6) is calculated by using the first target values calculated in step S200. The first correction coefficient group is a group of coefficients used for adjusting the measured values in the light-receiving device 16-$i$ to Vim, and accordingly, the coefficients are calculated as follows.

$$(a1A, a1C, a1B) = (V1m/V1A, V1m/V1C, V1m/V1B)$$

$$(a2A, a2C, a2B) = (V2m/V2A, V2m/V2C, V2m/V2B)$$

$$(a3A,a3C,a3B)=(V3m/V3A,V3m/V3C,V3m/V3B)$$

$$(a4A,a4C,a4B)=(V4m/V4A,V4m/V4C,V4m/V4B)$$

$$(a5A,a5C,a5B)=(V5m/V5A,V5m/V5C,V5m/V5B)$$

$$(a6A,a6C,a6B)=(V6m/V6A,V6m/V6C,V6m/V6B)$$

By multiplying each of the measured values of the light amount outputs in the light-receiving device 16-$i$ by a corresponding one of the coefficients included in the first correction coefficient group, the measured values in the light-receiving device 16-$i$ are adjusted to Vim.

In the next step S204, a second target value is calculated. The second target value is a target value used for further adjusting the measured values in the light-receiving devices 16, the measured values in each of the light-receiving devices 16 having been adjusted to a fixed value, to a single value. In the first exemplary embodiment, as the second target value, a maximum value Vm of the adjusted values Vim in the light-receiving devices 16, that is, the first target values, is used. A specific value Vm in the example illustrated in FIG. 9D is Vm=V3C. However, the second target value is not limited to a maximum value. Any one of the minimum value among the values Vim, the average value of the values Vim, the median value of the values Vim, and the like may be used in a method of calculating the second target value, and it is not necessary to use a method the same as the method of calculating the first target values.

In the next step S206, a second correction coefficient group (bi) (i=1 to 6) is calculated by using the second target value calculated in step S204. The second correction coefficient group is a group of coefficients used for further adjusting the values Vim in the light-receiving devices 16, the measured values in each of the light-receiving devices 16 having been adjusted to a fixed value, to the single value Vm, and accordingly, the coefficients are calculated as follows.

$$(b1,b2,b3,b4,b5,b6)=(Vm/V1m,Vm/V2m,Vm/V3m,Vm/V4m,Vm/V5m,Vm/V6m)$$

In the next step S208, a shading correction coefficient group (ciA, ciC, ciB) (i=1 to 6) used for adjusting all of the measured values in the light-receiving devices 16 to a single value is calculated. In other words, the shading correction coefficient group (ciA, ciC, ciB) (i=1 to 6) is calculated in the following manner from the calculation results obtained in step S202 and step S206.

$$(c1A,c1C,c1B)=(b1 \cdot a1A,b1 \cdot a1C,b1 \cdot a1B)$$

$$(c2A,c2C,c2B)=(b2 \cdot a2A,b2 \cdot a2C,b2 \cdot a2B)$$

$$(c3A,c3C,c3B)=(b3 \cdot a3A,b3 \cdot a3C,b3 \cdot a3B)$$

$$(c4A,c4C,c4B)=(b4 \cdot a4A,b4 \cdot a4C,b4 \cdot a4B)$$

$$(c5A,c5C,c5B)=(b5 \cdot a5A,b5 \cdot a5C,b5 \cdot a5B)$$

$$(c6A,c6C,c6B)=(b6 \cdot a6A,b6 \cdot a6C,b6 \cdot a6B)$$

After these coefficients have been calculated, the process returns to step S116 of the correction-processing program illustrated in FIG. 10.

Note that, although the case where the inclination angle $\theta$ of the correction mirror 50 is obtained beforehand has been described as an example in the above first exemplary embodiment, in the case where the inclination angle $\theta$ that causes light to be incident on the light-receiving device 16-$i$ is unknown, a method such as that described below may be used in order to calculate the inclination angle $\theta$ beforehand. That is to say, one of the light-emitting devices 12 is caused to emit light, and the inclination angle $\theta$ of the correction mirror 50 is continuously varied within a range sufficient to cause the light to be received by all of the light-receiving devices 16 of the light-receiving unit 18, that is, within a range of an inclination angle $\theta$m sufficient to cause the light to be received by the light-receiving device 16-1 illustrated in FIGS. 9A to 9C to an inclination angle $-\theta$m sufficient to cause the light to be received by the light-receiving device 16-6. Then, each time the inclination angle $\theta$ is varied, the light amount outputs in the light-receiving devices 16 are read so as to correspond to the inclination angle $\theta$. As a result, measured values that are similar to those illustrated in FIG. 9D and that correspond to the light-emitting device 12 are obtained, and thus, angles each of which corresponds to one of the light-receiving devices 16 are calculated from the measured values. It is obvious that, in the case where the light-receiving devices 16, which are arranged in a planar form as illustrated in FIG. 4A, are the measurement targets, two angles ($\theta\alpha$ and $\theta\beta$) with respect to two axes $\alpha$ and $\beta$ are calculated. In this manner, the inclination angle $\theta$ that is to be set in the above-described correction-processing program is obtained beforehand.

Although the case where the light-emitting devices 12 are caused to sequentially emit light after the inclination angle $\theta$ of the correction mirror 50 has been set when measuring the light amount outputs of the light-emitting devices 12 in each of the light-receiving devices 16 has been described as an example in the above first exemplary embodiment, the present invention is not limited to this case. Results similar to those illustrated in FIG. 9D may also be obtained by performing, on each of the light-emitting devices 12, an operation of causing one of the light-emitting devices 12 to emit light and then sequentially setting the inclination angle $\theta$ of the correction mirror 50 to predetermined angles. In the case where the inclination angle $\theta$ of the correction mirror 50 that is to be set for each of the light-receiving devices 16 is unknown, results similar to those illustrated in FIG. 9D may also be obtained by performing, on each of the light-emitting devices 12, an operation of causing one of the light-emitting devices 12 to emit light and then continuously varying the inclination angle $\theta$ of the correction mirror 50. Therefore, shading correction coefficients may be calculated by the subroutine for shading-correction-coefficient calculation processing illustrated in FIG. 11 using the measurement results.

In addition, although the case where the light amount outputs measured in each of the light-receiving devices 16 have no distribution (the case where each measured value is a fixed value) has been described as an example in the above first exemplary embodiment, in the case where each of the light-receiving devices 16 has a sensitivity distribution in its light-receiving surface and where each of the light amount outputs is measured in the form of a distribution, for example, the peak value of the distribution may be employed.

Furthermore, although the case where correction of the light emitting and light receiving systems is performed by shading correction has been described as an example in the above first exemplary embodiment, the present invention is not limited to this case. For example, measured values in each of the light-receiving devices 16 may be adjusted to a single value by changing the value of a drive current for each of the light-emitting devices 12 instead of by using the first correction coefficient group.

As described in detail above, according to the measuring device 10 according to the first exemplary embodiment, correction of the light emitting and light receiving systems is performed with a simple configuration in which the correction mirror 50 is caused to rotate. Therefore, the correction mirror 50 may be included in the measuring device 10 as standard equipment in such a manner as to be used at the time of product shipment of the measuring device 10 and to be used for applications such as correction and calibration that are performed by a user after the shipment.

Second Exemplary Embodiment

A measuring device 10A according to the second exemplary embodiment will now be described with reference to FIG. 12. In the second exemplary embodiment, the precision with which correction of light emitting and light receiving systems is performed is improved compared with in the above-described measuring device 10 according to the first exemplary embodiment. The measuring device 10A includes a diaphragm 40A having an aperture 42B instead of the diaphragm 40 of the measuring device 10, the diameter of the aperture 42B being smaller than that of the aperture 42 of the diaphragm 40. The same components as in the first exemplary embodiment are denoted by the same reference numerals, and repeated descriptions thereof will be omitted.

Figure 12:
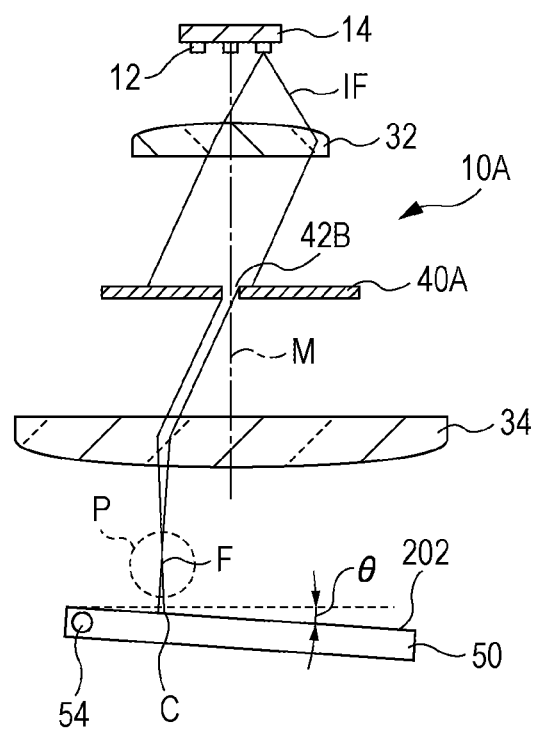
FIG. 12 is a diagram illustrating an exemplary configuration of a measuring device according to a second exemplary embodiment.

As illustrated in FIG. 12, a pencil of irradiation light rays IF that has passed through the diaphragm 40A has a fixed width and is diffused while having a fixed angular width even after being converged by the lens 34. In other words, as indicated by a dashed circle P in FIG. 12, the pencil of irradiation light rays IF that has passed through the diaphragm 40A is diffused while having a fixed angular width after being converged once at a focal point F of the lens 34 and is incident on the surface 202 of the correction mirror 50 at an incident point C. In the second exemplary embodiment, the angular width is about 1 degree.

Thus, the angles at which the irradiation light rays IF are reflected by the correction mirror 50 have an error (uncertainty) equal to the above-mentioned angular width. Consequently, in the measuring device 10A, in the case where it is desired to measure a finer inclination difference and a finer reflection-angle distribution, it is necessary to further reduce the diameters of the pencil of irradiation light rays IF and the pencil of reflected light rays RF.

Accordingly, in the measuring device 10A, by replacing the diaphragm 40 of the above-described measuring device 10 with the diaphragm 40A having an aperture 42B, whose diameter is smaller than that of the aperture 42 of the diaphragm 40, the pencil of irradiation light rays IF that has passed through the diaphragm 40A is further reduced in diameter. More specifically, although the aperture diameter of the diaphragm 40 of the measuring device 10 is about 1 mm, the aperture diameter of the diaphragm 40A of the measuring device 10A is set to 1 mm or less (e.g., about 0.5 mm). As a result, the pencil of reflected light rays RF is further reduced in diameter, and consequently, correction of the light emitting and light receiving systems may be performed with higher precision. As a method of replacing the diaphragm 40 with the diaphragm 40A, the diaphragm 40A may be prepared separately from the diaphragm 40, and the diaphragm 40 may be replaced with the diaphragm 40A when the correction of the light emitting and light receiving systems is performed. Alternatively, the diaphragm 40 may be configured in such a manner that the diameter of the aperture 42 is adjustable.

Here, by reducing the diameter of the aperture 42B of the diaphragm 40A, there is a possibility that the amount of the irradiation light IF, that is, the amount of the reflected light RF may be reduced and may be too small to be received by the light-receiving devices 16 with their light-receiving sensitivities. Thus, it is desirable that an adjustable range of the diameter of the aperture 42B be set by using the minimum light-receiving sensitivity of the light-receiving devices 16 as a lower limit.

Note that, although the configuration of the light-emitting unit 14 in which the light-emitting devices 12 are arranged in only one row in one direction has been described as an example in the first and second exemplary embodiments, the light-emitting unit 14 is not limited to this configuration and may have a configuration in which the light-emitting devices 12 are arranged in plural rows. In addition, in this case, the light-emission wavelengths of the light-emitting devices 12 may differ on a row-by-row basis. By causing the light-emitting devices 12 to emit light while the light-emission wavelengths of the light-emitting devices 12 differ on a row-by-row basis, for example, the wavelength dependence of the reflected light rays RF on the surface 200 of the object OB is measured.

In addition, although the case where the lens 32 and the lens 34 are convex lenses each having a substantially circular shape has been described as an example in the first and second exemplary embodiments, the lens 32 and the lens 34 are not limited to such convex lenses, and other types of lenses such as, for example, aspheric lenses may be used. Furthermore, in each of the lens 32 and the lens 34, an unnecessary portion through which a pencil of light rays will not pass may be removed.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A measuring device comprising:
   a light-emitting unit that emits irradiation light rays to be radiated onto an object;
   a first lens that changes a degree of divergence of each of the irradiation light rays emitted by the light-emitting unit;
   a diaphragm having an aperture that reduces a diameter of each of the irradiation light rays emitted from the first lens;
   a second lens that converges each of the irradiation light rays, which have passed through the aperture, and radiates the irradiation light ray onto the object in a predetermined direction;
   a light-receiving unit that is disposed between the diaphragm and the second lens and that receives at least part of reflected light rays corresponding to the irradiation light rays that have been radiated onto and reflected by the object and that have passed through the second lens;

a measuring unit that measures the object by using light-receiving results related to the light-receiving unit;

a reflector that is disposed as a replacement for the object and whose inclination angle with respect to the irradiation light rays emitted from the second lens is adjustable; and a correction unit that causes the irradiation light rays to be received by the light-receiving unit at different light-receiving positions by varying the inclination angle of the reflector with respect to the irradiation light rays and that performs correction of amounts of the irradiation light rays emitted by the light-emitting unit and correction of a light-receiving sensitivity of the light-receiving unit by using light-receiving results obtained at the light-receiving positions.

2. The measuring device according to claim 1, wherein the light-emitting unit includes a plurality of light-emitting devices that are arranged in a direction crossing the predetermined direction, wherein the light-receiving unit includes a plurality of light-receiving devices that are arranged in a plane crossing the predetermined direction, and wherein the correction unit causes the plurality of light-emitting devices to sequentially emit the irradiation light rays at different angles, each of which corresponds to the inclination angle, measures amounts of the irradiation light rays that have been emitted by the plurality of light-emitting devices and that have been received by each of the plurality of light-receiving devices, and performs the correction of the amounts of the irradiation light rays emitted by the light-emitting unit and the correction of the light-receiving sensitivity of the light-receiving unit by using the amounts of the received irradiation light rays, which have been measured.

3. The measuring device according to claim 2, wherein the correction unit calculates coefficients each of which is used for equalizing the amounts of the irradiation light rays that have been emitted by the plurality of light-emitting devices and that have been received by each of the plurality of light-receiving devices and performs the correction of the amounts of the irradiation light rays emitted by the light-emitting unit and the correction of the light-receiving sensitivity of the light-receiving unit simultaneously.

4. The measuring device according to claim 2, wherein a distance between light-receiving surfaces of the plurality of light-receiving devices and the second lens is set to be equal to a focal length of the second lens.

5. The measuring device according to claim 1, wherein the reflector is a reflector having a mirror surface.

6. The measuring device according to claim 1, wherein a size of the aperture is adjustable.

7. The measuring device according to claim 1, wherein a distance between the aperture and the first lens is set to be equal to a focal length of the first lens, and wherein a distance between the aperture and the second lens is set to be equal to a focal length of the second lens.

8. A non-transitory computer readable medium storing a program causing a computer to execute a process, the process comprising:

measuring an object by using light-receiving results related to a light-receiving unit; and causing irradiation light rays to be received by the light-receiving unit at different light-receiving positions by varying an inclination angle of a reflector with respect to the irradiation light rays and performing correction of amounts of the irradiation light rays emitted by a light-emitting unit and correction of a light-receiving sensitivity of the light-receiving unit by using light-receiving results obtained at the light-receiving positions.

* * * * *